US007048706B2

(12) United States Patent
Cea

(10) Patent No.: US 7,048,706 B2
(45) Date of Patent: May 23, 2006

(54) HYPOALLERGENIC BANDAGE

(76) Inventor: Beverly V. Cea, 5305 Guida Dr., Greensboro, NC (US) 27410

( * ) Notice: Subject to any disclaimer, the term of this patent is extended or adjusted under 35 U.S.C. 154(b) by 0 days.

(21) Appl. No.: 10/453,735

(22) Filed: Jun. 4, 2003

(65) Prior Publication Data
US 2004/0049144 A1 Mar. 11, 2004

Related U.S. Application Data

(60) Provisional application No. 60/409,598, filed on Sep. 11, 2002.

(51) Int. Cl.
A61F 5/00 (2006.01)
(52) U.S. Cl. .......................... 602/26; 128/882
(58) Field of Classification Search ................ 206/440, 206/441; 602/41–44, 52–59, 46, 48; 128/888, 128/889; 424/443–449; 604/304–308
See application file for complete search history.

(56) References Cited

U.S. PATENT DOCUMENTS

| 3,811,438 A | * | 5/1974 | Economou | 602/55 |
| 4,333,471 A | * | 6/1982 | Nakai | 450/81 |
| 4,393,150 A | * | 7/1983 | Kresner | 523/111 |
| 4,631,227 A | | 12/1986 | Nakamura | |
| 4,838,273 A | | 6/1989 | Cartmell | |
| 4,915,102 A | * | 4/1990 | Kwiatek et al. | 604/307 |
| 4,930,500 A | | 6/1990 | Morgan | |
| 5,042,466 A | | 8/1991 | McKnight | |
| 5,250,043 A | | 10/1993 | Castellana et al. | |
| 5,368,553 A | | 11/1994 | Newman | |
| 5,586,971 A | | 12/1996 | Newman | |
| 5,772,623 A | | 6/1998 | Conte | |
| 5,792,091 A | | 8/1998 | Staudinger | |
| 6,124,522 A | | 9/2000 | Schroeder | |
| 6,277,458 B1 | | 8/2001 | Dirksing et al. | |
| 2003/0143261 A1 | * | 7/2003 | Noda et al. | 424/443 |

FOREIGN PATENT DOCUMENTS

| CN | 1277831 | 12/2000 |
| WO | WO 00/02506 | * 1/2000 |

OTHER PUBLICATIONS

Shilog Medical Supplies & Equipment, "Esmarch Latex-Free Bandage," printed from the Internet on Apr. 22, 2003.

* cited by examiner

Primary Examiner—Kim Lewis
(74) Attorney, Agent, or Firm—Richard C. Litman

(57) ABSTRACT

A bandage which may be used to cover, protect and promote the healing of wounds, lacerations and the like on the skin of a human or animal allergic or sensitive to latex. The bandage has a hypoallergenic layer with a contact surface, an adhesive on the contact surface, and a dressing attached to the contact surface. The hypoallergenic layer may be made of paper. The bandage may further comprise a strip of wax paper to protect the adhesive and the dressing. In order to prevent the contamination of the bandage, the bandage may be adapted to be contained in a sterile container so that the bandage is provided in a pre-packaged and ready-to-use form that is preferred by consumers and medical professionals. The bandage may be provided in any suitable shape or size.

7 Claims, 5 Drawing Sheets

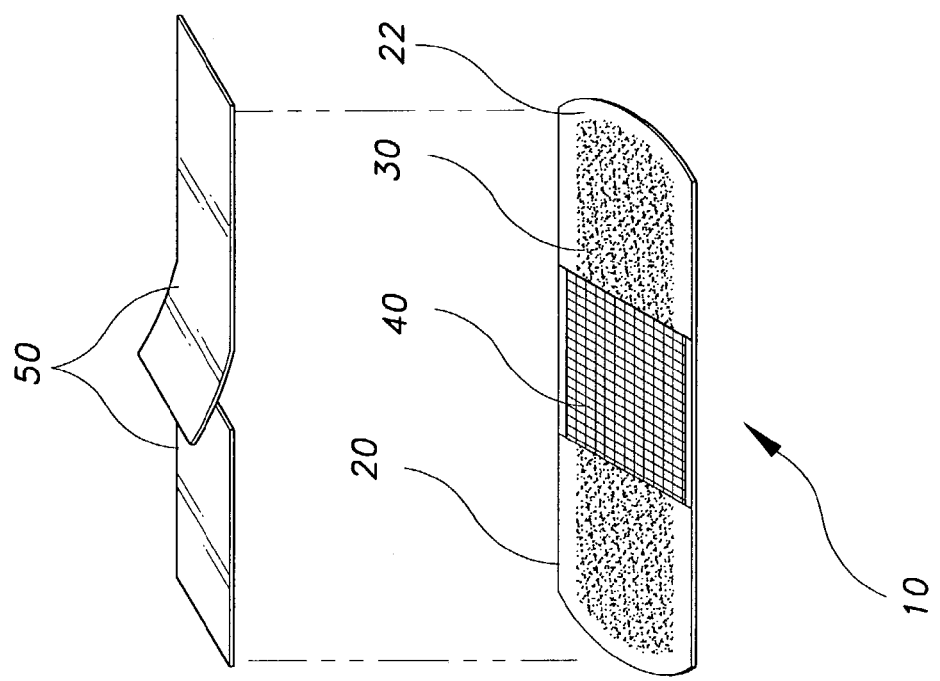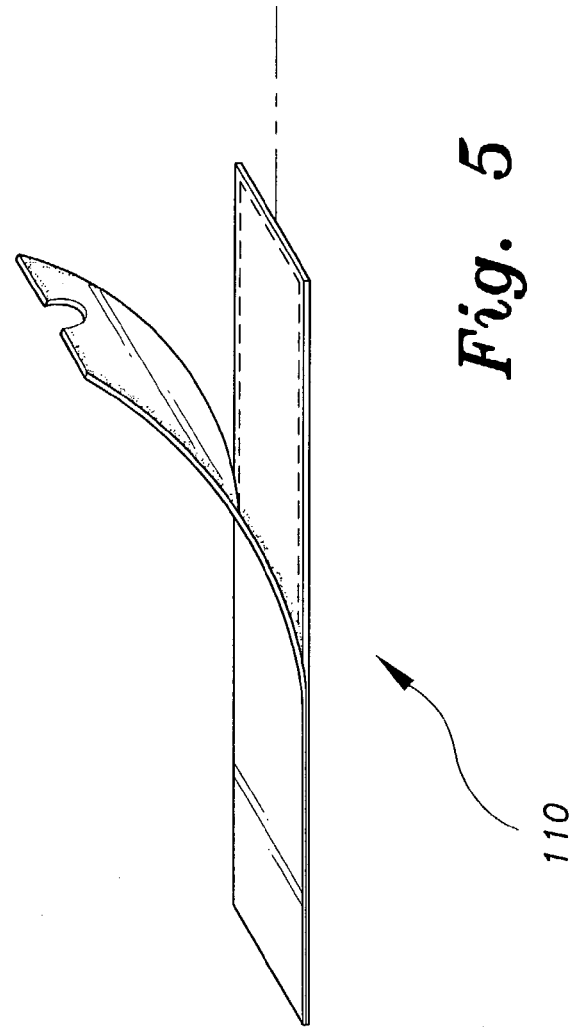
Fig. 5

HYPOALLERGENIC BANDAGE

CROSS-REFERENCE TO RELATED APPLICATION

This application claims the benefit of U.S. Provisional Patent Application Ser. No. 60/409,598, filed Sep. 11, 2002.

BACKGROUND OF THE INVENTION

1. Field of the Invention

The present invention relates to a hypoallergenic bandage, particularly a hypoallergenic bandage adapted for use on the skin of a human or animal allergic or sensitive to latex.

2. Description of Related Art

About 1–2% of the general population is sensitive to latex. About 15–20% of health care workers are latex sensitive. If latex is exposed to the skin of a latex sensitive person, the result can be a poison-ivy like rash on the skin to respiratory distress. In extreme cases, a severe latex reaction may result in life-threatening anaphylactic shock. Small children, older people that may require frequent bandages, surgery patients, and patients receiving IVs may be particularly susceptible to latex allergies.

Conventional pre-packaged, ready-to-use bandages are commonly made from latex. For the reasons discussed above, a latex sensitive person cannot safely or comfortably use these bandages. If it is determined that a person is latex sensitive, the customary alternative treatment is to create and apply a custom wound dressing. This process exposes the dressing to germs and contaminants, requires several time-consuming steps and wastes both dressing material and the material used to attach the dressing to the skin. First, a piece of wound dressing material, such as gauze, must be cut into an appropriate sized piece with scissors or a cutting implement. Then, the shaped material is placed on the wound. Often, latex sensitive patients are asked to merely hold the dressing on the wound. If available, strips of hypoallergenic tape are used to attach the dressing to the skin. The hypoallergenic tape is provided in a roll which must be dispensed and cut to fit the wound dressing, again with scissors or a cutting implement. When cutting the gauze to size and the tape from the roll, the gauze and tape are exposed to germs and contaminants on the hands of the person dispensing the tape and on the scissors. Sometimes, due to the extra time involved in creating a custom dressing, the patient simply is not properly bandaged.

A variety of devices have been proposed for dressing wounds; however, none are known to address the particular concerns of latex sensitive patients.

U.S. Pat. No. 5,586,971, issued Dec. 24, 1996 to Newman discloses an invisible bandage assembly with a micro-pore type paper backing to which make-up is applied that matches the skin tone of the person to whom the assembly is applied. U.S. Pat. No. 6,124,522, issued Sep. 26, 2000 to Schroeder discloses a packaging for adhesive-sided articles to allow one-handed application with a backing sheet that may be made of paper. Newman and Schroeder do not teach or suggest a hypoallergenic bandage, latex sensitivity, or providing the bandage in a prepackaged, ready-to-use form.

Other patents showing devices for use on the skin include U.S. Pat. No. 4,838,273, issued Jun. 13, 1989 to Cartmell (medical electrode with circular shape); and U.S. Pat. No. 6,277,458, issued Aug. 21, 2001 to Dirksing et al. (release strip with adhesive coated strips that may be made of paper).

None of the above inventions and patents, taken either singly or in combination, is seen to describe the instant invention as claimed.

SUMMARY OF THE INVENTION

The present invention is a bandage which may be used to cover, protect and promote the healing of wounds, lacerations and the like on the skin of a human or animal. The bandage comprises a hypoallergenic layer with a contact surface, an adhesive on the contact surface, and a dressing attached to the contact surface. The hypoallergenic layer may be a paper hypoallergenic layer. The hypoallergenic layer may be adapted for use on the skin of the human or animal allergic or sensitive to latex. The bandage may further comprise a strip of wax paper to protect the adhesive and the dressing. In order to prevent the contamination of the bandage, the bandage may be adapted to be contained in a sterile container. By providing the bandage in the sterile container, the bandage is provided in a pre-packaged and ready-to-use form that is preferred by consumers and medical professionals. The bandage may be provided in any suitable shape and size.

Accordingly, it is a principal object of the invention to provide a hypoallergenic bandage.

It is another object of the invention to provide a hypoallergenic bandage which is pre-packaged and ready-to-use.

It is a further object of the invention to provide a hypoallergenic paper bandage.

Still another object of the invention is to provide a hypoallergenic bandage which is suitable for use with a human or animal sensitive to latex.

It is another object of the invention to provide a hypoallergenic bandage with a strip of wax paper to protect said adhesive and said dressing.

It is a further object of the invention to provide a hypoallergenic bandage which is adapted to be contained in a sterile container.

Still another object of the invention is to provide a hypoallergenic bandage which has a generally rectangular shape.

It is another object of the invention to provide a hypoallergenic bandage which has a generally circular shape.

It is a further object of the invention to provide a hypoallergenic bandage which has a generally triangular shape.

Still another, object of the invention is to provide a prepackaged, ready-to-use bandage package with a sterile container, a hypoallergenic bandage for a human or animal sensitive to latex, where said hypoallergenic bandage is disposed inside said container.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 5 is an environmental, perspective view of a hypoallergenic bandage which is insertable into a sterile container.

Similar reference characters denote corresponding features consistently throughout the attached drawings.

DETAILED DESCRIPTION OF THE PREFERRED EMBODIMENTS

Figure 1:
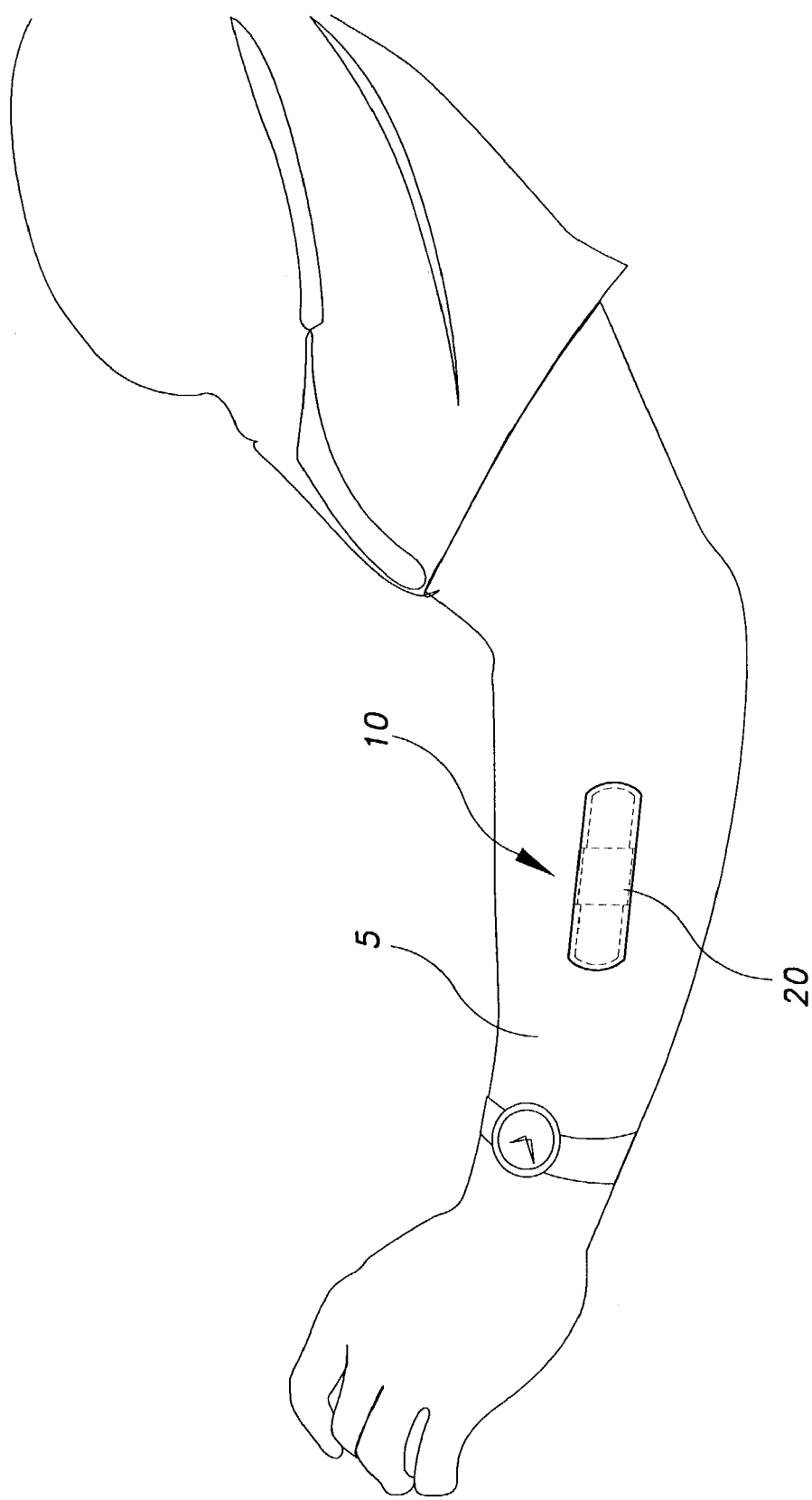
FIG. 1 is an environmental, perspective view of a hypoallergenic bandage for human or animal allergic or sensitive to latex according to the present invention.
Figure 2:
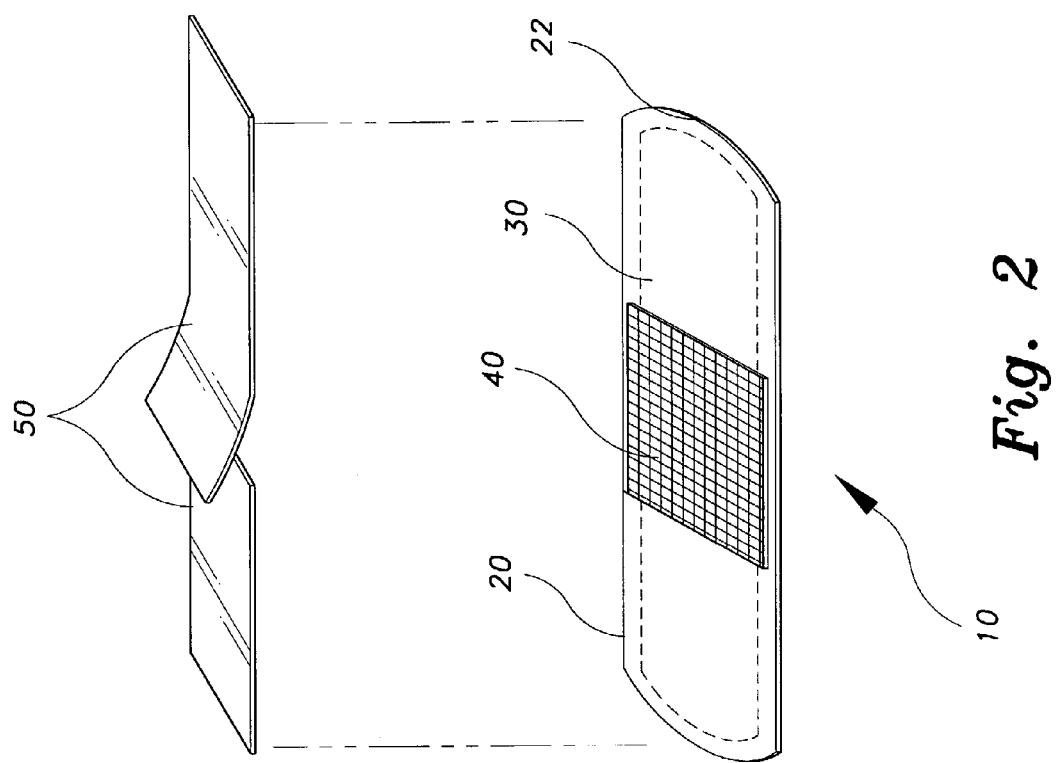
FIG. 2 is an environmental, perspective view of a hypoallergenic bandage with a generally rectangular shape.
Figure 3:
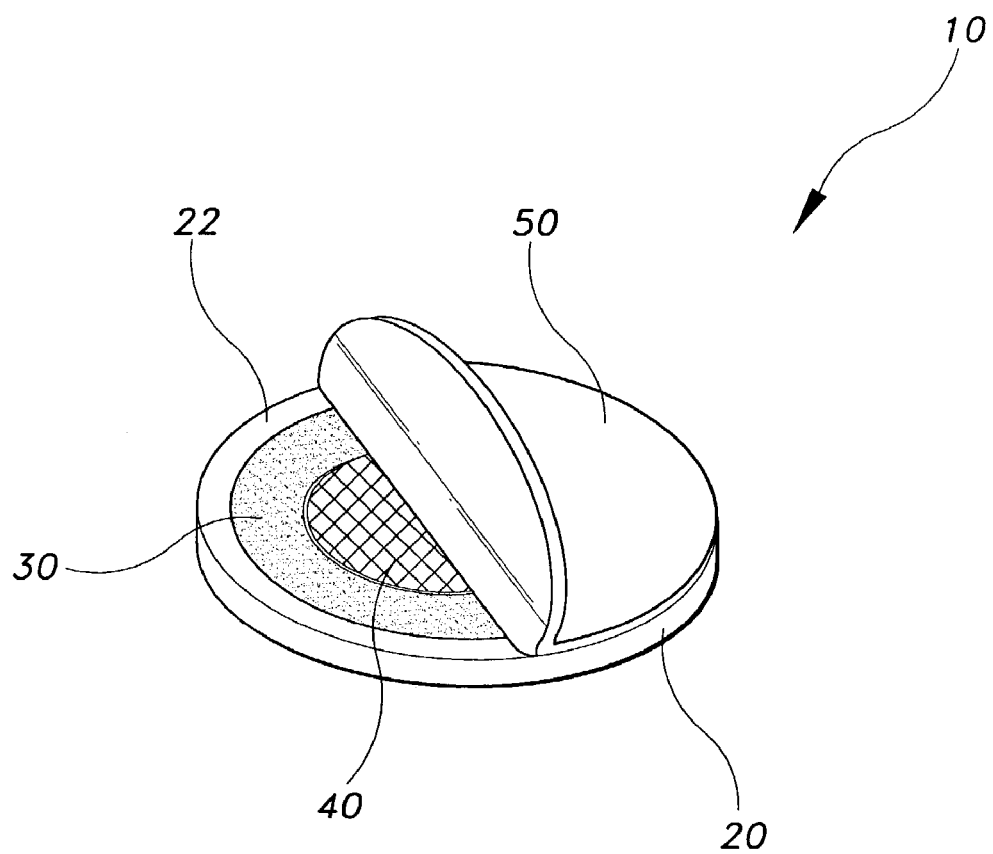
FIG. 3 is an environmental, perspective view of a hypoallergenic bandage with a generally circular shape.
Figure 4:
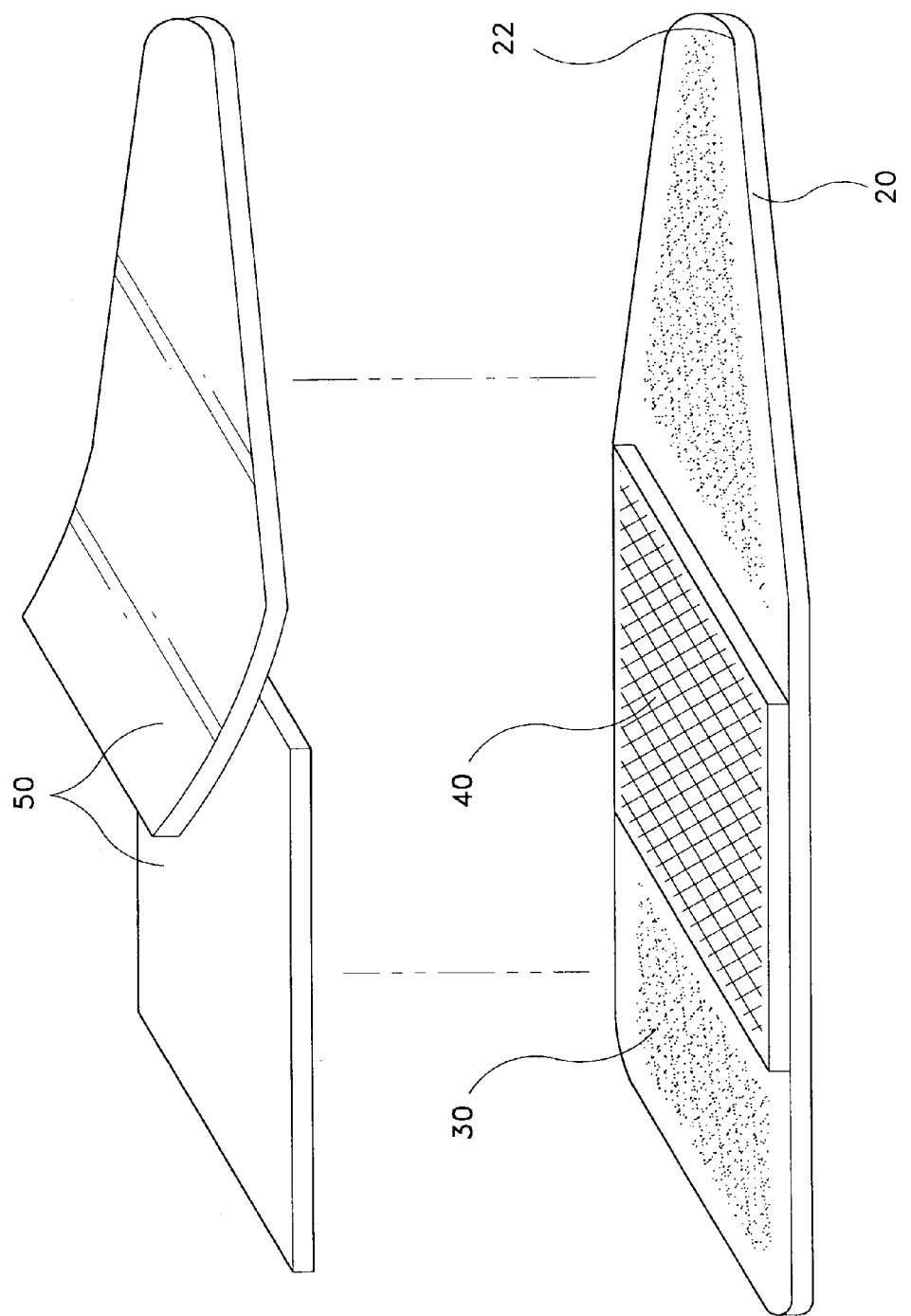
FIG. 4 is an environmental, perspective view of a hypoallergenic bandage with a generally triangular shape.

The present invention is a bandage, designated generally as 10 in the drawings. As seen in FIG. 1, the bandage 10 may be used to cover, protect and promote the healing of wounds, lacerations and the like on the skin of a human or animal 5. As seen in FIGS. 2-4, the bandage 10 comprises a hypoallergenic layer 20 with a contact surface 22, an adhesive 30 on the contact surface 22, and a dressing 40 attached to the contact surface 22. The hypoallergenic layer 20 may be made of any material, such as paper, which is suitable for use on the skin of the human or animal 5 allergic or sensitive to latex including natural latex, artificial latex, latex-containing substances and the like. The adhesive 30 may be any adhesive suitable for temporarily attaching the hypoallergenic layer 20 to the skin of the human or animal 5. The dressing 40 may be any suitable material which has absorptive properties, promotes healing, and will not adversely affect a wound on the skin of the human or animal 5. The bandage 10 may further comprise a strip of wax paper 50 to protect the adhesive 30 and the dressing 40. In order to prevent the contamination of the bandage 10, the bandage 10 may be adapted to be contained in a sterile container 110, such as a sterile wax paper container. The bandage 10 may be provided in any suitable shape or size.

As seen in FIG. 2 in a first embodiment of the invention, the bandage 10 may have a generally rectangular shape. The rectangular bandage may be about 7.5 cm long and 2.5 cm wide with rounded ends; however, smaller or larger bandages may be provided. The rectangular bandage may be used to cover wounds, lacerations and the like. The dressing 40 for the rectangular bandage is roughly square in shape with about 2.5 cm sides. The size of the dressing 40 varies for smaller or larger bandages.

As seen in FIG. 3 in a second embodiment of the invention, the bandage 10 may have a generally circular shape. The circular bandage may be about 3.0 cm in diameter with a smaller diameter dressing 40; however, smaller or larger bandages may be provided. Circular bandages may be used for smaller puncture wounds, lacerations and the like.

As seen in FIG. 4 in a third embodiment of the invention, the bandage 10 may have a generally triangular shape. The triangular bandage is about 8.0 cm long and 2.5 cm long at one end tapering to about 0.5 cm at the other end; however, smaller or larger bandages may be provided. The triangular bandage may be used for fingers and toes.

For the purposes of sale, safe storage and transport of the bandage 10, it may be desirable to provide a bandage package comprising the bandage 10 as described above in a sterile container 110 (FIG. 5). The sterile container 110 may be made of any suitable material, such as strips of sterile wax paper which are adhered together to form a pocket for the bandage 10 which can be temporarily sealed until the bandage 10 is needed. In providing the bandage 10 in the sterile container 110, the bandage 10 is provided in a pre-packaged and ready-to-use form that is preferred by consumers and medical professionals.

It is to be understood that the present invention is not limited to the sole embodiments described above, but encompasses any and all embodiments within the scope of the following claims.

I claim:

1. A hypoallergenic bandage consisting essentially of:
   a hypoallergenic paper carrier layer having a contact surface and an exterior surface;
   an adhesive disposed on said contact surface;
   a dressing fixedly attached to said carrier layer, said dressing being substantially centrally located on said contact surface;
   at least one strip of wax paper releasably adhered to said adhesive on said contact surface of said paper carrier layer for covering and protecting said adhesive and said dressing; and
   a sterile wax paper container designed and configures to store and maintain said bandage in a sterile state:
   wherein said paper carrier layer, said adhesive, said dressing, and said at least one strip of wax paper are sterile and adapted to be packaged for single use;
   whereby, application of said hypoallergenic bandage to a skin surface for covering an open wound provides a reduced risk of reaction to latex allergens.

2. The bandage according to claim 1, wherein said bandage has a generally rectangular shape.

3. The bandage according to claim 1, wherein said bandage has a generally circular shape.

4. The bandage according to claim 1, wherein said bandage has a generally triangular shape.

5. A hypoallergenic skin coverage kit consisting essentially of:
   a bandage including a hypoallergenic paper carrier layer, an adhesive, a dressing, and at least one cover strip;
   said paper carrier layer having a contact surface and an exterior surface;
   said adhesive disposed on said contact surface;
   said dressing fixedly attached to said paper carrier layer, said dressing being substantially centrally located on said contact surface;
   said at least one cover strip being releasably adhered to said adhesive on said contact surface of said paper carrier layer for covering and protecting said adhesive and said dressing;
   wherein said at least one cover strip is formed of sterile wax paper, and
   a container for storing and containing said bandage;
   wherein said container stores and maintains said bandage in a sterile state such that said paper carrier layer, said adhesive, said dressing and said at least one cover strip are sterile and are packaged for single use in said container;
   whereby, upon applying said hypoallergenic bandage to a skin surface for covering an open wound , a reduced risk of reaction to latex allergens is provided.

6. The hypoallergenic skin coverage kit according to claim 5, wherein said bandage has a generally rectangular shape.

7. The hypoallergenic skin coverage kit according to claim 5, wherein said bandage has a generally circular shape.

* * * * *